United States Patent [19]

Lawrence et al.

[11] Patent Number: 5,770,545

[45] Date of Patent: Jun. 23, 1998

[54] A2,6-DINITROANILINE HERBICIDE

[75] Inventors: Lowell J. Lawrence; Terry L. Johnson; Stephan Kwiatkowski, all of Lexington, Ky.; Paul D. Smith, Seabrook, Tex.

[73] Assignee: SRM Chemical, Ltd. Co., League City, Tex.

[21] Appl. No.: 818,541

[22] Filed: Mar. 14, 1997

[51] Int. Cl.$^6$ ............ A01N 33/18; C07C 211/00
[52] U.S. Cl. .............................. 504/347; 564/441
[58] Field of Search ............... 564/441; 504/347

[56]  References Cited

U.S. PATENT DOCUMENTS

| | | | |
|---|---|---|---|
| 3,111,403 | 11/1963 | Soper | 504/183 |
| 3,257,190 | 6/1966 | Soper | 504/347 |
| 3,332,769 | 7/1967 | Soper | 504/347 |
| 3,518,076 | 6/1970 | Wright | 504/143 |
| 3,518,309 | 6/1970 | Soper | 564/411 |
| 3,672,866 | 6/1972 | Damiano | 504/183 |
| 3,927,127 | 12/1975 | Damiano | 568/933 |
| 3,991,116 | 11/1976 | Damiano | 564/411 |
| 4,025,538 | 5/1977 | Lutz et al. | 564/87 |
| 4,066,441 | 1/1978 | Lutz et al. | 504/347 |
| 4,119,669 | 10/1978 | Levy et al. | 564/44 |
| 4,166,908 | 9/1979 | Lutz et al. | 544/166 |
| 4,297,127 | 10/1981 | Lutz et al. | 504/224 |

*Primary Examiner*—Deborah C. Lambkin
*Attorney, Agent, or Firm*—Arnold, White & Durkee

[57]  ABSTRACT

This invention relates to pendralin [2,6-dinitro-N-(1-ethylpropyl)-4-tert-butylaniline], preemergence and postemergence herbicidal methods and herbicidal compositions employing pendralin.

20 Claims, No Drawings

A 2,6-DINITROANILINE HERBICIDE

BACKGROUND OF THE INVENTION

1. Field of the Invention

This invention relates to a novel substituted 2,6-dinitroaniline compound, preemergence and postemergence herbicidal methods, and compositions.

2. Description of Related Art

N-alkyl-dinitroalkylanilines such as N-sec-butyl-4-tert-butyl-2,6-dinitroaniline [(1,1-dimethylethyl)-N-(1-methylpropyl)-2,6-dinitrobenzenamine; butralin] are known selective herbicides generally used for preemergence control of annual broad-leaved weeds and grasses in cotton, soybeans, rice, barley, beans, alliums, vines, ornamentals and orchards of fruit and nut trees. They are also used to control suckers of tobacco.

Among the dinitroaniline derivatives which have found commercial acceptance as preemergence herbicides are N-(1-ethylpropyl)-2,6-dinitro-3,4-xylidine, also known as pendimethalin, and N-sec-butyl-4-tert-butyl-2,6-dinitroaniline, also known as butralin. Compounds of this type are disclosed for example in U.S. Pat. Nos. 3,991,116; 4,025,538; and 4,166,908. In spite of the good herbicidal activity of these dinitroaniline compounds, some are not sufficiently selective in their activity and too often they also affect adversely the host crop plants. In addition, a lower effective application rate of herbicide than required for said compounds currently available is more advantageous from the standpoint of limiting environmental exposure.

Among the 2,6-dinitroaniline compounds of the prior art having a branched alkyl group attached to the amino group, 3- and 4-carbon chains are favored over chains of longer length. In accordance with this invention it has been found that notwithstanding the experience with 2,6-dinitroaniline compounds wherein alkyl groups of shorter length are preferred for herbicidal effectiveness there can be obtained a herbicidally active compound of unusually high activity and particularly good selectivity in a variety of agronomic crops when a branched alkyl group of 5 carbons is introduced to the amino group.

SUMMARY OF THE INVENTION

The present invention provides a novel compound, [2,6-dinitro-N-(1-ethylpropyl)-4-tert-butylaniline] termed pendralin herein, which is a highly effective preemergent and postemergent herbicide.

The present invention also provides preemergence and postemergence herbicidal methods and compositions employing pendralin.

DESCRIPTION OF ILLUSTRATIVE EMBODIMENTS

The invention relates to pendralin, a novel substituted 2,6-dinitroaniline compound, and preemergence and postemergence herbicidal methods and compositions employing pendralin.

Pendralin is a compound of the formula:

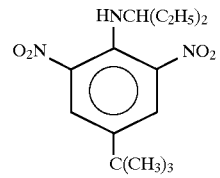

The above-identified compound is a highly effective preemergent and postemergent herbicidal agent and may be used to control a wide variety of undesirable monocotyledonous and dicotyledonous plants.

The herbicidal methods of the invention comprise application of a herbicidally effective amount of pendralin either to the soil containing the seeds of undesirable plant species to be controlled for preemergent control or to said undesirable plants for postemergent control.

Preferably, application of this compound, or active ingredient is made using the herbicidal compositions described below with conventional application methods.

Pendralin is prepared by reacting a dinitro-substituted alkylanisole with an amine to produce the desired N-alkyl-dinitroalkylaniline product. More specifically, 2,6-dinitro-4-tert-butylanisole is reacted with 1-ethylpropyl-amine to produce 2,6-dinitro-N-(1-ethylpropyl)-4-tert-butylaniline, which is graphically illustrated below. Other methods of preparation are disclosed in the patent literature, e.g. U.S. Pat. Nos. 3,672,866; 3,927,127; 3,991,116; and 4,289,907.

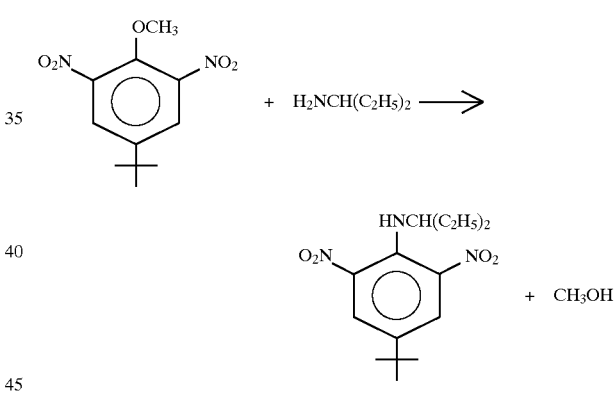

More specifically describing the reaction, substantially 25.8 g of 2,6-dinitro-4-tert-butylanisole, DNTBA (98.5% pure, 0.1 mole), is introduced into a 200 mL round bottom flask equipped with a reflux condenser followed by substantially 25 mL of methanol and substantially 17.8 mL of 1-ethylpropyl-amine (98% pure, 0.15 mole). The resulting mixture is heated to reflux with stirring for about seven hours. The contents of the flask are then cooled in an ice-bath and the resulting orange-yellow crystals are filtered off and vacuum dried yielding substantially 27.2 g (87.8% yield) of the final product, pendralin: mp 45–47 C; $^1$H NMR (2 mg, 0.7 mL CDCl$_3$) δ ppm: 0.86 t (6H, 2×—CH$_3$), 1.30 s (9H, —C(CH$_3$)$_3$), 1.50 m (4H, 2×—CH$_2$—), 3.07 m (1H, —CH—), 7.90 sbr (1H, —NH—), 8.08 s (2H, ring H). The product is substantially 99.7% pure and contains about 0.25% of 2,4-dinitro-N-(1-ethylpropyl)aniline and about 0.05% of two unidentified impurities. An additional amount of the product, substantially 2.2 g (7.1% yield, 98.9% pure) is separated after concentrating a filtrate to the volume of substantially 5 mL. The combined yield is about 94.6% with a purity of about 99.6%.

The preemergence herbicidal compositions of the present invention are solid or liquid formulations comprising an effective amount of pendralin. Preparation of the compositions broadly involves admixing an effective amount of the herbicidal agent and adjuvant, according to the general procedure described below.

Use of the compositions broadly involves application of an effective amount of the compound or preferably the composition to the soil containing seeds of the plants to be controlled or directly to the plants to be controlled.

Typical formulations include, for example, emulsifiable concentrates, dust concentrates, wettable powders, granulars, and the like. Application by conventional methods and equipment is usually made at rates of from about 1/8 pound per acre to about 20 pounds per acre of active material.

Emulsifiable concentrates are generally prepared by combining approximately 1% to 50% by weight of the active material with an organic solvent such as light naphtha. In addition, there is generally added about 1% to 5% by weight of a surfactant such as polyoxyethylene alcohols, acids, adducts, sorbitan fatty acid esters and sorbitol esters.

Dust concentrates are generally prepared by grinding together from about 15% to 95% by weight of the active material with from about 85% to 5% by weight of a solid diluent, such as an attaclay, kaolin, diatomaceous earth, fullers earth, talc, pumice or the like.

Granular formulations may be prepared by applying a liquid solution of the active material to sorptive granular carriers, such as attaclay, kaolin, or diatomite granules. Alternatively, they may be mixed with inert carriers and applied to non-sorptive granules, such as sand or limestone.

Wettable powders are prepared by grinding the active ingredient with a solid carrier, such as used in the dust formulations. Usually, about 25% to 75% by weight of the active material and from about 73% to 23% by weight of solid carrier is used. In addition, there is generally added about 1% to 5% by weight of a dispersing agent, such as alkali metal salts of naphthalene sulfuric acid and anionic-nonionic blends, and from about 1% to 5% by weight of a surfactant, such as polyoxyethylene alcohols, acids, adducts, sorbitan fatty acid esters and sorbitol esters.

The wettable powder formulations are usually dispersed in water and applied as a liquid spray to the area or locus where control of undesirable plant species is desired.

For use as preemergence herbicides, the dusts or liquid sprays containing the active compound can be applied to the soil shortly after planting or they may be incorporated into the soil by the technique referred to as preplant incorporation.

Preliminary data clearly show that pendralin is an effective herbicide. In comparison with the commercial products butralin and pendimethalin, it displays equal or superior activity toward certain weeds such as crabgrass, even at the reduced application rate of about one pound per acre, with less injury to the host crop. This is particularly true for wheat, soybeans, lettuce and turnips.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The selective preemergence herbicidal activity of pendralin is exemplified by the following tests in which soil is treated with pendralin dissolved in acetone at rates equivalent to about 1 to 4 pounds per acre of pendralin. The soil is then placed in 10"×20" planting flats and planted with seeds of several species of monocotyledonous and dicotyledonous plants. The plants are allowed to grow about two weeks. Plants grown in treated soil are compared to the same species grown in control (solvent-treated) soil for size and stand. The test results are reported in the Tables I and II below.

TABLE I

Pre-Emergence Activity: Trial 1-Weed Species

| Treatment Rate | Plant Size (mm) | | | | |
|---|---|---|---|---|---|
| | Crabgrass | | Pigweed | Foxtail | Velvet Leaf |
| | Replicate 1 | Replicate 2 | | | |
| Control | 109 | 100 | 140 | 95 | 147 |
| 1 lb./acre | 10 | 5 | 23 | 43 | 143 |
| 2 lbs./acre | <5$^a$ | <5$^a$ | 13$^b$ | 35 | 130 |
| 4 lbs./acre | <5$^a$ | <5$^a$ | <6$^a$ | <5 | 97 |

$^a$Stand reduced by ≧70% of control.
$^b$Stand reduced by ≧50% of control.

TABLE II

Pre-Emergence Activity: Trial 1-Crop Species

| Treatment Rate | Plant Size (mm) | | | | |
|---|---|---|---|---|---|
| | Lettuce | Turnip | Wheat | Sorghum | Soybean |
| Control | 47 | 80 | 267 | 260 | 273 |
| 1 lb./acre | 47 | 92 | 267 | 177 | 267 |
| 2 lbs./acre | 37 | 82 | 237 | 157 | 257 |
| 4 lbs./acre | 17 | 53 | 180 | 130 | 240 |

EXAMPLE 2

The superiority of the selective preemergence herbicidal activity of pendralin over other commercially available 2,6-dinitroaniline compounds is exemplified by the following tests in which soil is treated with pendralin dissolved in acetone at rates equivalent to about 1 to 4 pounds per acre of pendralin, or soil is treated with either pendimethalin or butralin dissolved in acetone at rates of about 2 pounds per acre of the compound. The soil is then placed in 10"×20" planting flats and planted with seeds of several species of monocotyledonous and dicotyledonous plants. The plants are allowed to grow about two weeks. Plants grown in treated soil are compared to the same species grown in control (solvent-treated) soil for size and stand. The test results are reported in the Tables II and IV below.

TABLE III

Pre-Emergence Activity: Trial 2-Weed Species

| Treatment Rate | Plant Size (mm) | | | | |
|---|---|---|---|---|---|
| | Crabgrass | | Pigweed | Foxtail | Velvet Leaf |
| | Replicate 1 | Replicate 2 | | | |
| Control | 27 | 27 | 67 | 50 | 62 |
| Pendimethalin (2 lbs./acre) | <7[a] | 7[a] | 7[b] | <5[b] | 27 |
| Butralin (2 lbs./acre) | <5 | <5 | 10 | 17 | 35 |
| Pendralin 1 lb./acre | <5 | <5 | 13 | 28 | 55 |
| 2 lbs/acre | <5[a] | <5[a] | 10 | 13 | 43 |
| 4 lbs./acre | <5[a] | <5[a] | 5[b] | <5 | 30 |

[a]Stand reduced by ≧70% of control.
[b]Stand reduced by ≧50% of control.

TABLE IV

Pre-Emergence Activity: Trial 2-Crop Species

| Treatment Rate | Plant Size (mm) | | | | |
|---|---|---|---|---|---|
| | Lettuce | Turnip | Wheat | Sorghum | Soybean |
| Control | 18 | 70 | 193 | 197 | 267 |
| Pendimethalin (2 lbs./acre) | 8 | 28 | 63 | 38 | 207 |
| Butralin (2 lbs./acre) | 17 | 45 | 130 | 117 | 220 |
| Pendralin 1 lb./acre | 20 | 65 | 150 | 143 | 230 |
| 2 lbs./acre | 12 | 52 | 113 | 123 | 223 |
| 4 lbs./acre | 8 | 42 | 75 | 85 | 200 |

EXAMPLE 3

The postemergence herbicidal activity of pendralin is exemplified by the following test in which seedling plants (about 1.5 weeks post-germination) of two weed species are grown in 10"×20" planting flats. They are treated topically with a control formulation spray or the equivalent of about 2 or 4 pounds per acre of pendralin in a formulation spray. The formulation consists of the following: 94% organic solvent (Aromatic 200®, Exxon Chemical), 3% anionic emulsifier (Casol 55HF®, Harcross Co.), and 3% non-ionic emulsifier (T-DET C-40®, Harcross Co.). After adding the appropriate amount of pendralin to the formulation, it is diluted with water to produce the spray solution of appropriate concentration for application. Approximately one week after application, the plants are evaluated by comparing treated plants to control plants for size and stand. Vigor and apparent growth aberrations are also noted. The test results are reported in the table below.

TABLE V

Post-Emergence Activity

| Treatment Rate | Plant Size (mm) | | | | | |
|---|---|---|---|---|---|---|
| | Crabgrass | | | | Foxtail | |
| | Replicate | | | | | |
| | 1 | 2 | 3 | 4 | 1 | 2 |
| Control | 150 | 150 | 170 | 150 | 200 | 170 |
| 2 lbs./acre | 40[a,c] | 50[b] | 70[b,c] | 40[a,c] | 110 | 70[b] |
| 4 lbs./acre | 30[a,c] | 25[a,c] | 50[a,c] | 30[a,c] | 100[b] | 100 |

[a]Stand reduced by ≧70% of control.
[b]Stand reduced by ≧50% of control.
[c]Twisted, deformed.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A compound having the structure:

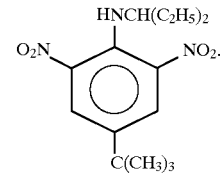

2. A method for the pre-emergence control of undesirable plant species comprising applying to soil containing seeds of the undesirable plant species at 4 pounds per acre or less of the compound of claim 1.

3. A method for the postemergence control of undesirable plant species comprising applying to the undesirable plant species a herbicidally effective amount of the compound of claim 1.

4. A herbicidal composition comprising an admixture of an inert herbicidal adjuvant and a herbicidally effective amount of the compound of claim 1.

5. The method of claim 2 wherein the quantity of the compound applied is 2 pounds per acre or less.

6. The method of claim 2 wherein the quantity of the compound applied is 1 pound per acre or less.

7. The method of claim 3 wherein the quantity of the compound applied is 4 pounds per acre or less.

8. The method of claim 3 wherein the quantity of the compound applied is 2 pounds per acre or less.

9. The method of claim 2 wherein the weeds to be controlled comprise crabgrass.

10. The method of claim 5 wherein the weeds to be controlled comprise crabgrass.

11. The method of claim 6 wherein the weeds to be controlled comprise crabgrass.

12. The method of claim 2 wherein the weeds to be controlled comprise foxtail.

13. The method of claim 5 wherein the weeds to be controlled comprise foxtail.

14. The method of claim 6 wherein the weeds to be controlled comprise foxtail.

15. The method of claim 2 wherein the weeds to be controlled comprise pigweed.

16. The method of claim 5 wherein the weeds to be controlled comprise pigweed.

17. The method of claim 6 wherein the weeds to be controlled comprise pigweed.

18. The method of claim 3 wherein the weeds to be controlled comprise crabgrass.

19. The method of claim 3 wherein the weeds to be controlled comprise foxtail.

20. The method of claim 5 wherein the crop comprises turnip, sorghum, or soybean.

* * * * *

UNITED STATES PATENT AND TRADEMARK OFFICE
CERTIFICATE OF CORRECTION

PATENT NO. : 5,770,545

DATED : June 23, 1998

INVENTOR(S) : Lowell J. Lawrence; Terry L. Johnson; Stephan Kwiatkowski; Paul D. Smith.

It is certified that error appears in the above-identified patent and that said Letters Patent is hereby corrected as shown below:

Title page, Item [54], and Col. 1, line 1:
In the title insert a space between the letter "A" and the number "2"

The title should read as follows: A 2,6-Dinitroaniline Herbicide

Signed and Sealed this

Fifteenth Day of September, 1998

Attest:

BRUCE LEHMAN

Attesting Officer

Commissioner of Patents and Trademarks